US012697407B1

(12) United States Patent
Sipes

(10) Patent No.: US 12,697,407 B1
(45) Date of Patent: Aug. 4, 2026

(54) MULTI-FUNCTION EQUIPMENT RACK FOR ELECTROCHEMICALLY ACTIVATED SOLUTIONS

(71) Applicant: Annihilare Medical Systems, Inc., Lincolnton, NC (US)

(72) Inventor: Clay Parker Sipes, Hickory, NC (US)

(73) Assignee: Annihilare Medical Systems, Inc., Lincolnton, NC (US)

( * ) Notice: Subject to any disclaimer, the term of this patent is extended or adjusted under 35 U.S.C. 154(b) by 385 days.

(21) Appl. No.: 18/516,919

(22) Filed: Nov. 21, 2023

(51) Int. Cl.
*A61L 2/18* (2026.01)
(52) U.S. Cl.
CPC ............. *A61L 2/18* (2013.01); *A61L 2202/11* (2013.01); *A61L 2202/15* (2013.01)
(58) Field of Classification Search
CPC ....................................................... A61L 2/18
See application file for complete search history.

(56) References Cited

U.S. PATENT DOCUMENTS

| | | | | |
|---|---|---|---|---|
| 2014/0001054 A1* | 1/2014 | Longhenry | ............. | C25B 15/00 |
| | | | | 204/232 |
| 2022/0143245 A1* | 5/2022 | Knatt | ......................... | A61L 2/10 |
| 2023/0313389 A1* | 10/2023 | Ben Salah | ................ | A01P 1/00 |
| | | | | 424/661 |

FOREIGN PATENT DOCUMENTS

DE 102010022841 A1 * 12/2011 ............... A61L 2/22

OTHER PUBLICATIONS

English Translation of Document Identification No. DE 102010022841 A1 provided by the European Patent Office website espacenet.com: Gurt; Arrangement Useful for Decontaminating Polluted Articles by E.g. Biological Hazardous Substances, Comprises a Block-shaped Frame . . . ; Dec. 8, 2011 (Year: 2011).*

* cited by examiner

*Primary Examiner* — Kevin Joyner
(74) *Attorney, Agent, or Firm* — CHRISTOPHER C. DREMANN, P.C.; Christopher C. Dremann

(57) ABSTRACT

A multi-function equipment rack is provided in a first Generation and Distribution Station Configuration for producing, storing and distributing electrochemically activated (ECA) solutions. The first Configuration of the equipment rack includes a stand, a brine tank, a water filter, a generator operable for producing the ECA solutions, ECA solution holding tanks and a dilution control station for diluting the ECA solutions to various strengths. A multi-function equipment rack is provided in a second Distribution Station Configuration for storing and distributing ECA solutions at a satellite location remote from a location where the ECA solutions are produced. The second Configuration of the equipment rack includes the stand, the ECA solution holding tanks and the dilution control station. The orientation of the stand is reversed in the second Configuration relative to the first Configuration such that the same stand can be used in either the first or second Configuration with minimal modifications.

19 Claims, 11 Drawing Sheets

MULTI-FUNCTION EQUIPMENT RACK FOR ELECTROCHEMICALLY ACTIVATED SOLUTIONS

FIELD OF THE INVENTION

The present invention relates generally to producing, storing and distributing electrochemically activated (ECA) solutions. More particularly, the present invention relates to an equipment rack for producing, storing and distributing effective cleaning, degreasing, sanitizing and disinfecting solutions. In an advantageous embodiment, the present invention is a multi-function equipment rack for a hypochlorous acid (HOCl) solution and a sodium hydroxide (NaOH) solution produced from an electrochemically activated water (EAW) process.

BACKGROUND OF THE INVENTION

Many facilities, including hospitals, nursing homes, prisons, schools and public terminals, are highly susceptible to multi-drug resistant organisms (MDROs), commonly referred to as infectious bacteria and viruses. For example, the Centers for Disease Control and Prevention (CDCP) estimates that infections acquired from healthcare and food service facilities kill more individuals each year than vehicle accidents, breast cancer or AIDS. As a result, the Environmental Protection Agency (EPA) and the Food and Drug Administration (FDA) prescribe effective cleaning and disinfecting procedures to be used in facilities that provide healthcare services and/or food services. In response, hospitals, nursing homes, prisons and schools have instituted detailed cleaning and disinfecting protocols along with intensive training programs for environmental services personnel to ensure that areas accessed by patients, staff and the public are clean and hygienic.

The aforementioned facilities, especially healthcare facilities, have historically utilized a variety of high, medium and low-level disinfectants, including formaldehyde, hydrogen peroxide, peracetic acid and chlorine-releasing agents (CRAs), including sodium hypochlorite, iodophor and phenol solutions. More recently, solutions of hypochlorous acid (HOCl) have been introduced as an efficacious and environmentally friendly alternative to traditional disinfectants. HOCl is a weak acid formed when chlorine dissolves in water and partially dissociates. Consequently, HOCl acts as an oxidizer and a primary disinfecting agent in a chlorine solution. The co-product of HOCl production from an EAW process is NaOH, which is useful as an effective cleaning and degreasing agent. The apparatus, system and method for producing HOCl solution and NaOH solution by the EAW process is commonly referred to as an HOCl/NaOH generator. An example ECA solutions generator for producing HOCl solution and NaOH solution from the EAW process is known from United States Patent Application Publication No. 2022/0396505 A1, the disclosure of which is incorporated herein by reference.

The beneficial characteristics attributed to HOCl include that it is a highly effective disinfectant for destroying infectious bacteria and viruses, most notably *C. diff*, E-*Coli*, MRSA (Staph), *Salmonella, Tuberculosis*, Human Immunodeficiency Virus (HIV), and Severe Acute Respiratory Syndrome (SARS). Despite being highly effective, HOCl is relatively harmless to humans at concentrations sufficient for effective sanitizing and disinfecting. Consequently, HOCl solutions are approved for use as sanitizers and disinfectants in hospitals, nursing homes, prisons, schools and public terminals. Other cleaning and disinfectant agents commonly used in such facilities are not as environmentally friendly or as effective as HOCl in destroying harmful and deadly bacteria and viruses. As a result, it is not uncommon for individuals to contract serious illnesses from the bacteria and viruses at those facilities that are treated with other disinfectants. The inability to effectively destroy infectious organisms increases healthcare costs and causes physical harm to individuals that could have been prevented with the use of the more effective HOCl sanitizing and disinfecting agent.

Although highly effective, HOCl has a relatively limited lifespan of effectiveness as a disinfectant, referred to commercially as its "shelf life." Over time HOCl decomposes to chloric acid, hydrochloric acid, and oxygen; none of which separately exhibits the same desirable disinfectant properties as a full strength HOCl solution. The shelf life for HOCl solution as a sanitizing and disinfecting agent is therefore time-sensitive from the moment the solution is produced based on its free available chlorine (FAC) concentration. As used herein, the term "free available chlorine (FAC)" is intended to mean the portion of total chlorine in the solution that is present as hypochlorous acid (HOCl) or hypochlorite ion (OCl—). Consequently, it is imperative to take steps to ensure that an effective HOCl disinfectant solution is being used by environmental services personnel with an approved cleaning and disinfecting protocol at facilities such as hospitals, nursing homes, prisons, schools and public terminals. In particular, it is essential that environmental services personnel use an HOCl solution that is within the life cycle of effectiveness that is acceptable for its cleaning, sanitizing and/or disinfecting purpose.

In view of the foregoing, it is apparent a need exists for an improved apparatus, system and method for producing, storing and distributing effective ECA solutions. A more particular need exists for an apparatus, system and method for producing effective cleaning, degreasing, disinfecting and sanitizing solutions. A specific need exists for a multi-function equipment rack for electrochemically activated solutions of hypochlorous acid (HOCl) and sodium hydroxide (NaOH) produced from an EAW process. Such an apparatus, system and method would necessarily ensure that an environmentally safe and effective HOCl sanitizing and disinfecting solution, as well as an effective NaOH cleaning and degreasing solution, is made readily available to environmental services personnel for convenient use with an approved cleaning and disinfecting protocol in compliance with EPA and FDA requirements.

Certain aspects, objects, features and advantages of the invention will be made apparent or will be readily understood and appreciated by those skilled in the relevant art, with reference to exemplary embodiments of the invention described herein and illustrated by the accompanying drawing figures. It is intended that the aspects, objects, features and advantages of the invention set forth herein be construed in accordance with the ordinary and customary meaning of the terms used in the appended claims given their broadest reasonable interpretation consistent with this written disclosure and accompanying drawing figures. Some or all aspects, objects, features and advantages of the invention, as well as others not expressly or inherently disclosed herein, may be accomplished by one or more of the exemplary embodiments provided herein. However, it should be appreciated that the written description and drawing figures are for illustrative purposes only, and that many modifications, substitutions or revisions may be made to the exemplary embodiments without departing from the general concepts of the invention and the intended broad scope, construction and interpretation of the appended claims.

BRIEF DESCRIPTION OF THE DRAWINGS

The aforementioned aspects, objects, features and advantages of the invention will be more fully understood and appreciated when considered with reference to the accompanying drawing figures, in which like reference characters designate the same or similar parts throughout the several views.

DETAILED DESCRIPTION OF EXEMPLARY EMBODIMENTS OF THE INVENTION

Exemplary embodiments of the present invention are described in greater detail and shown in the accompanying drawing figures. The present invention shown and described herein is directed to an apparatus, system and method for producing, storing and distributing ECA solutions. More particularly, the present invention is a multi-function equipment rack for producing, storing and distributing cleaning, degreasing, sanitizing and disinfecting solutions. In the exemplary embodiments shown and described herein, the present invention is a multi-function equipment rack for ECA solutions of HOCl and NaOH produced from an EAW process. The EAW process is a technology that produces a sanitizing and disinfecting non-synthetic and biodegradable biocide compound HOCl solution and a cleaning and degreasing agent NaOH solution utilizing an ECA solutions generator. An example ECA solutions generator for producing HOCl solution and NaOH solution is known from United States Patent Application Publication No. 2022/0396505 A1. The ECA solutions generator produces HOCl solution and NaOH solution from water, salt and electricity utilizing an electrolysis cell.

Various aspects, objects, features and advantages of the present invention are described and illustrated by exemplary embodiments of a multi-function equipment rack for producing, storing and distributing HOCl solution and NaOH solution. In an exemplary embodiment of the present invention illustrated in FIGS. 1-6 commercially known as and referred to herein as a "Generation and Distribution Station Configuration," an ECA solutions generator is mounted on the multi-function equipment rack for producing HOCl solution and NaOH solution locally at facilities such as hospitals, nursing homes, prisons, schools and public terminals. Consequently, the HOCl solution having a limited shelf life can be produced on-site in a suitable amount and at a suitable interval to ensure the effectiveness of the HOCl solution. In another exemplary embodiment of the present invention illustrated in FIGS. 7-9 commercially known as and referred to herein as a "Distribution Station Configuration," containers of HOCl solution and NaOH solution are mounted on the multi-function equipment rack for storing and distributing the ECA solutions in a convenient manner at a location, commonly referred to as a satellite location, that is remote from the location where the HOCl solution and the NaOH solution were produced. In either embodiment, a dilution control station may be mounted on the multi-function equipment rack for diluting the HOCl solution and/or the NaOH solution to a desired parts-per-million (PPM) level various strengths of cleaning, degreasing, sanitizing and disinfecting solutions.

Figure 1:
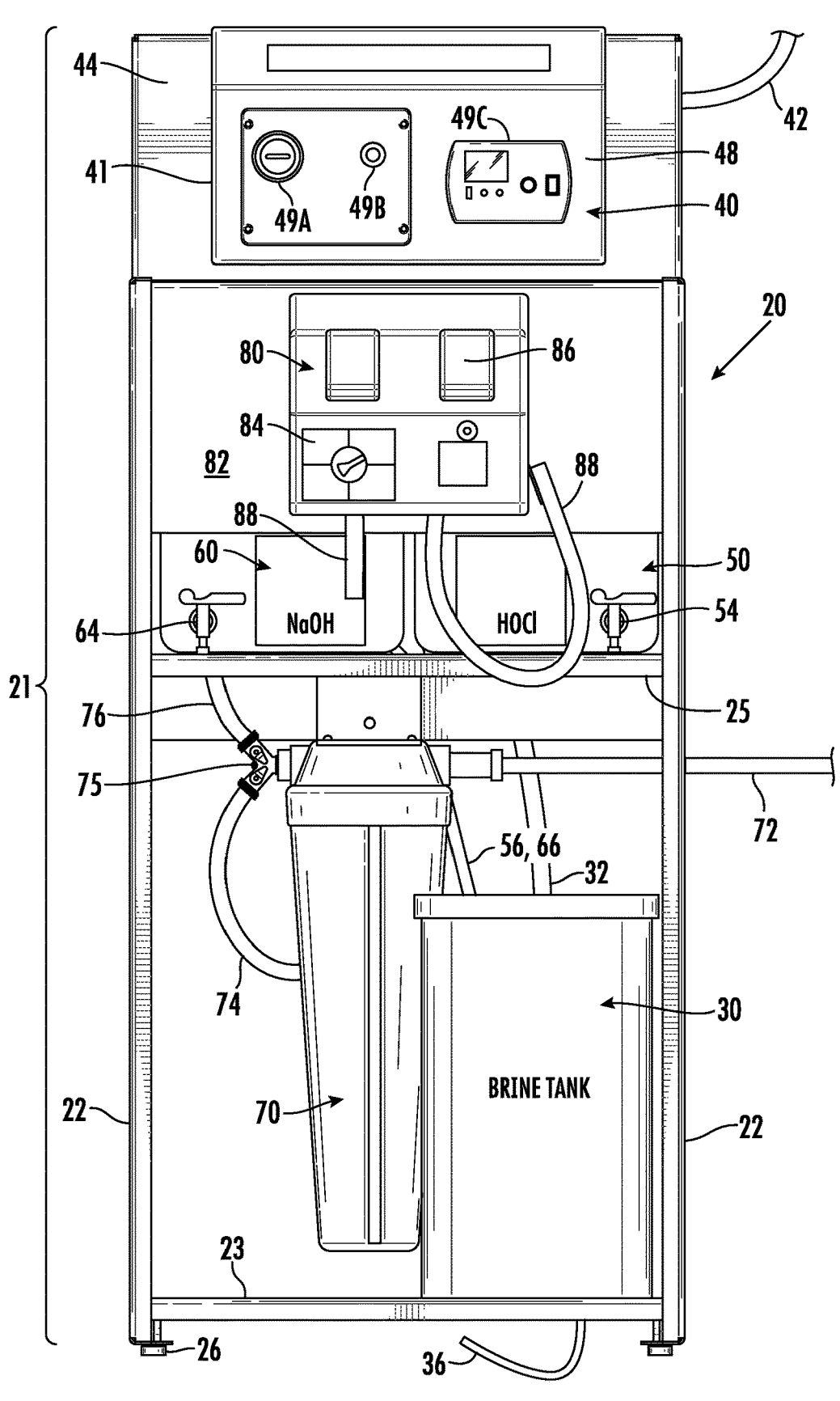
FIG. 1 is a front elevation view of an exemplary embodiment of a multi-function equipment rack for producing, storing and distributing ECA solutions according to the present invention.
Figure 2:
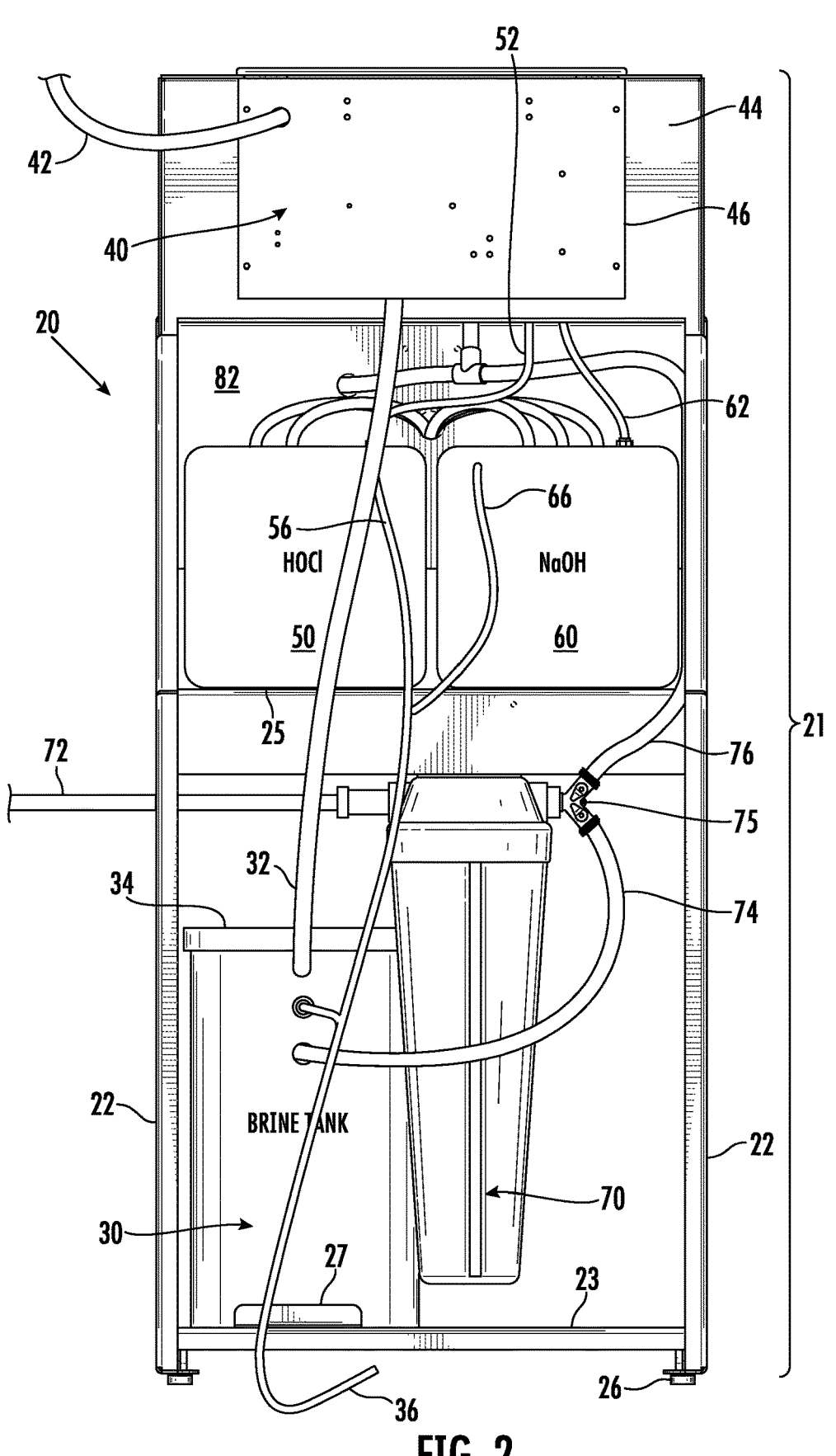
FIG. 2 is a rear elevation view of the multi-function equipment rack of FIG. 1.
Figure 3:
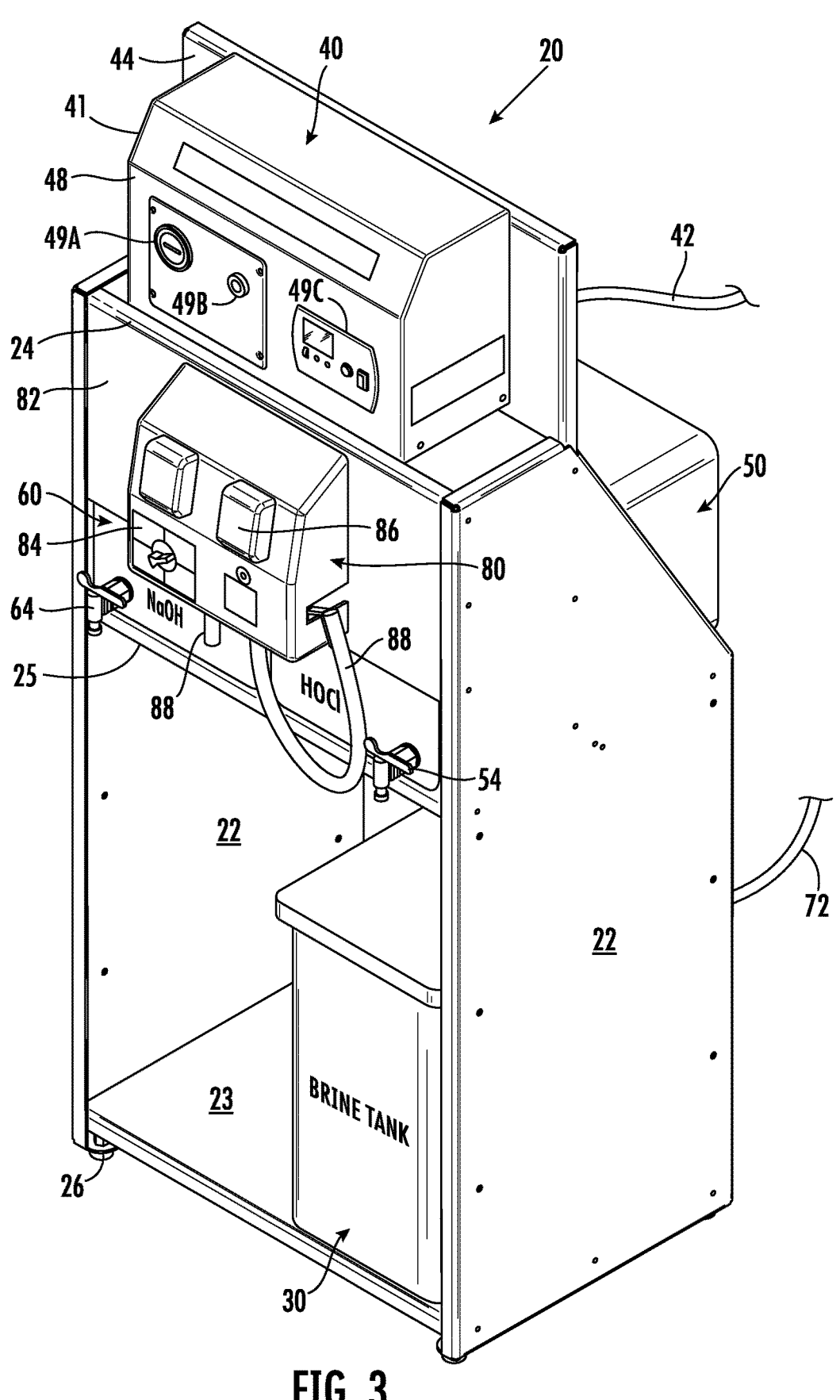
FIG. 3 is a front perspective view of the multi-function equipment rack of FIG. 1.
Figure 4:
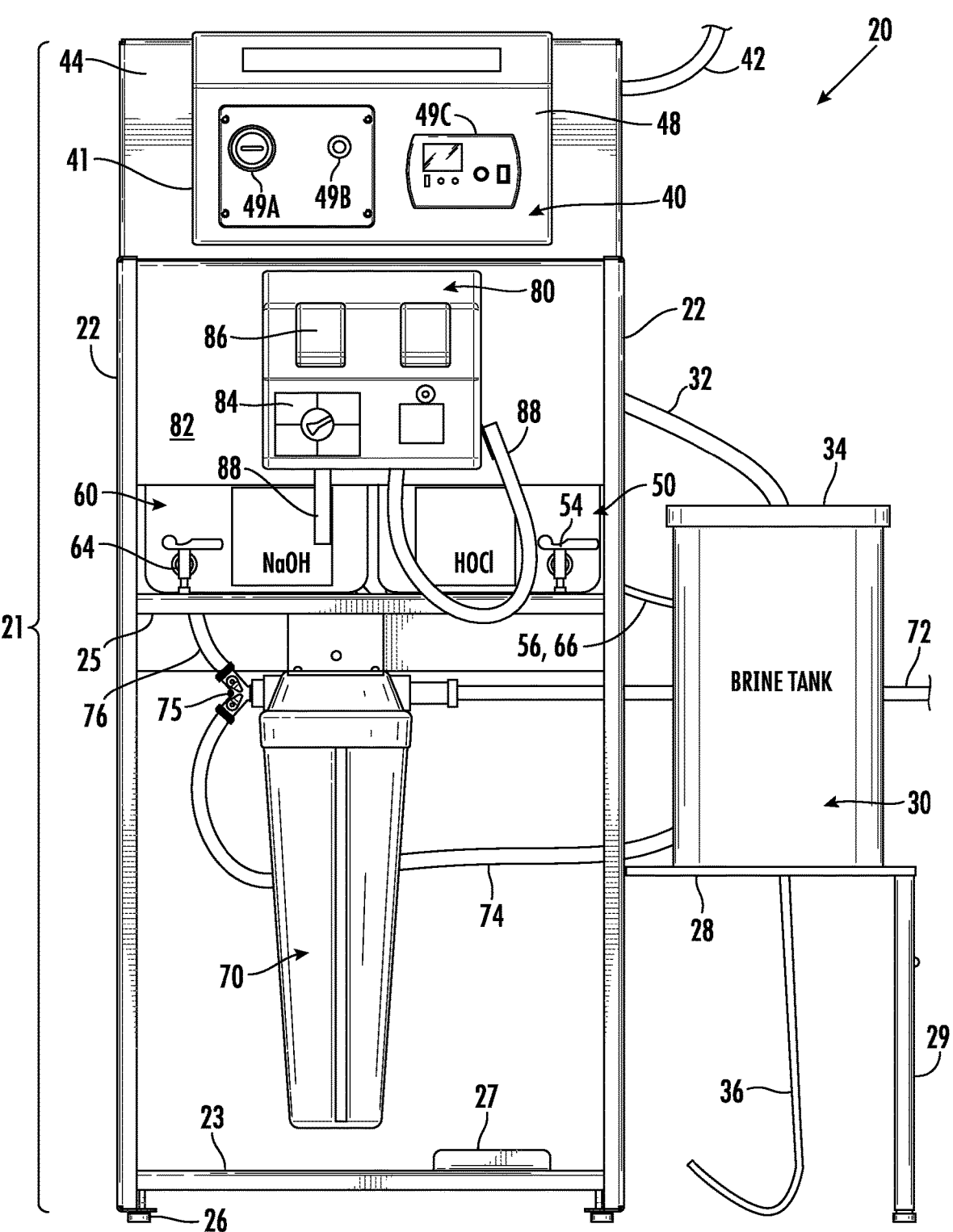
FIG. 4 is a front elevation view of the multi-function equipment rack of FIG. 1 shown in an alternative arrangement.
Figure 5:
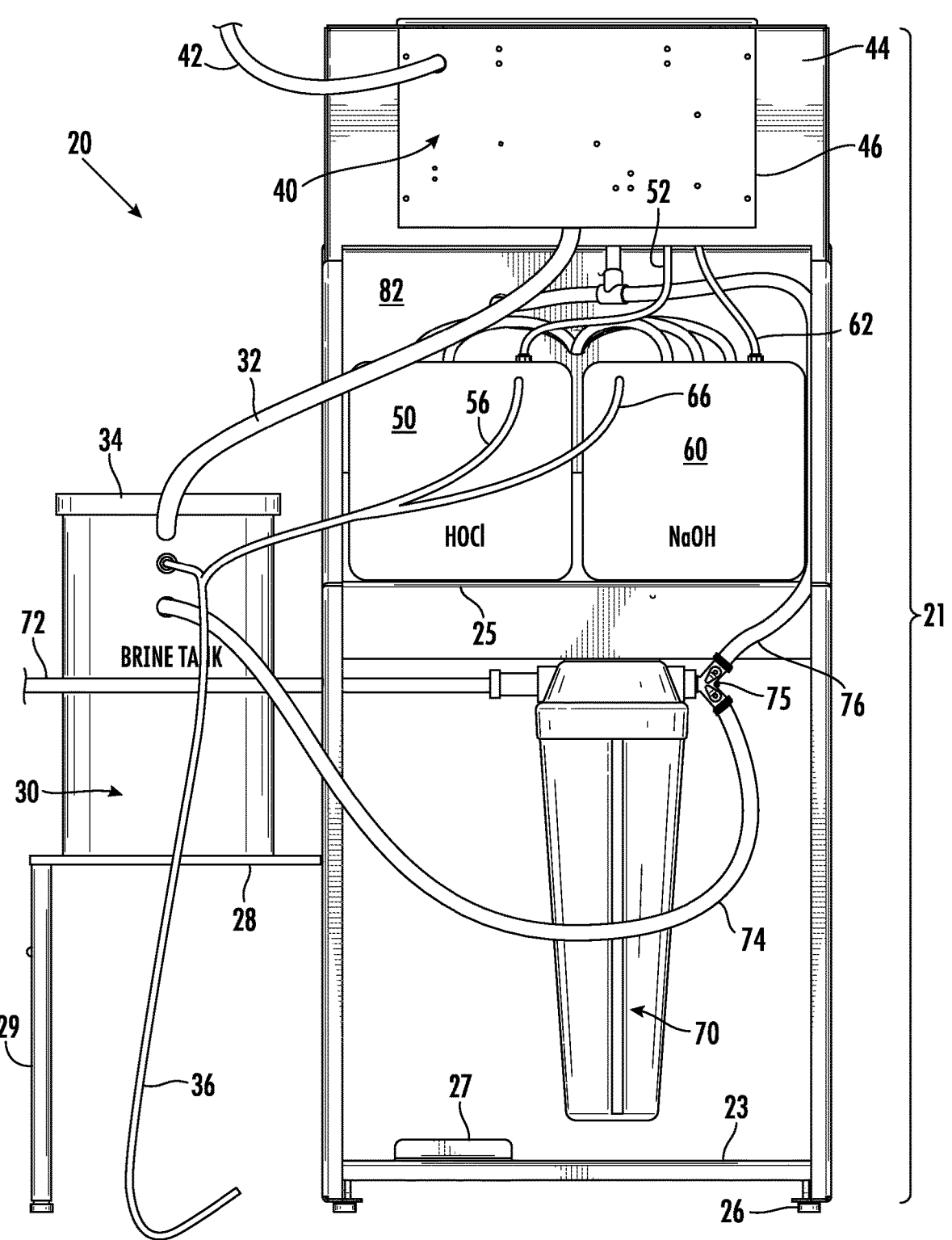
FIG. 5 is a rear elevation view of the multi-function equipment rack of FIG. 1 shown in the alternative arrangement.
Figure 6:
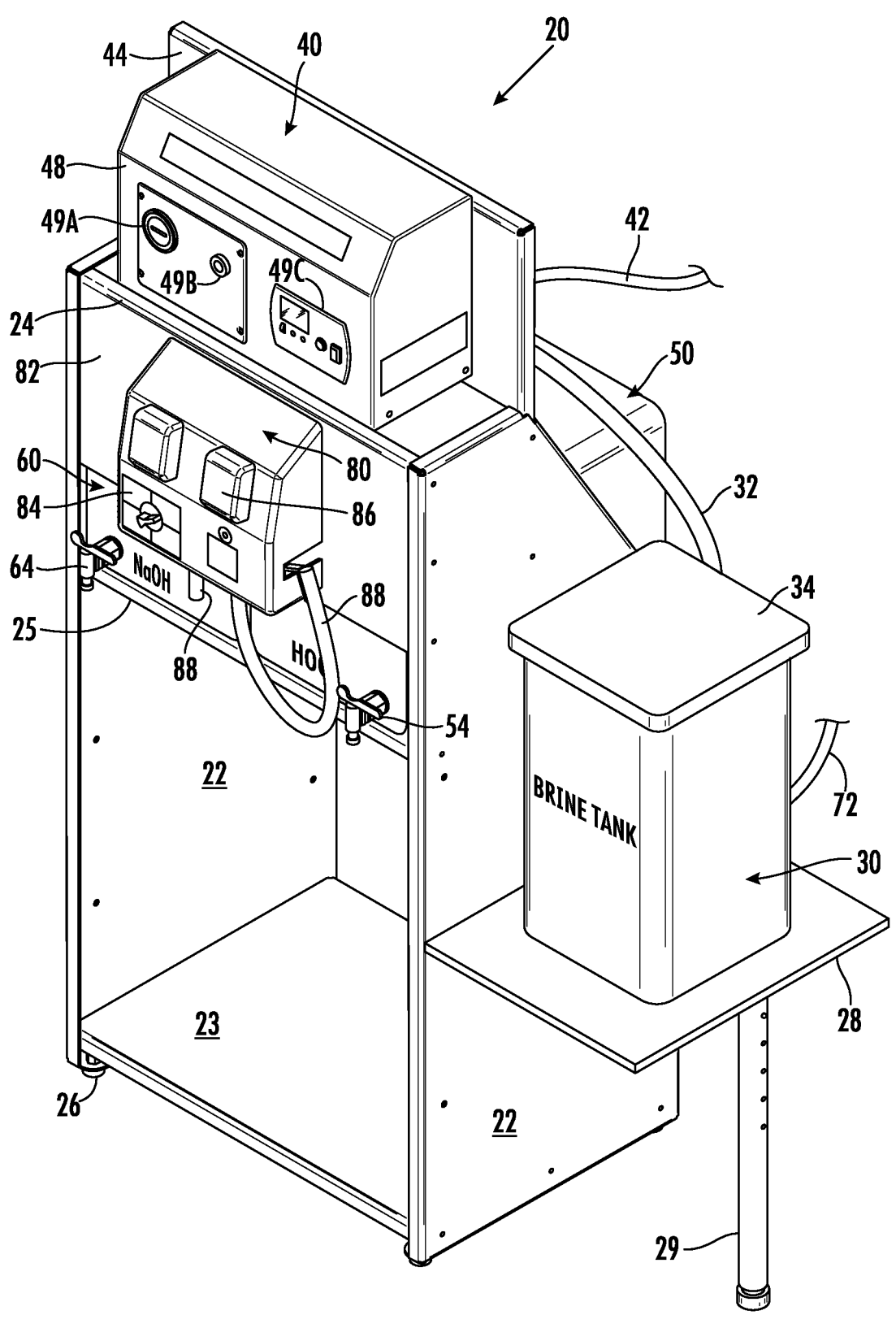
FIG. 6 is a front perspective view of the multi-function equipment rack of FIG. 1 shown in the alterative arrangement.

FIGS. 1-6 show an exemplary embodiment of an apparatus, system and method for producing, storing and distributing ECA solutions according to the present invention. Specifically, FIGS. 1-6 illustrate a multi-function equipment rack, indicated generally by reference character 20, in the Generation and Distribution Station Configuration for producing, storing and distributing HOCl solution and NaOH solution from an EAW process. For purposes of reference herein, FIGS. 1 and 4 are front elevation views, FIGS. 2 and 5 are rear elevation views, and FIGS. 3 and 6 are front perspective views in the Generation and Distribution Station Configuration of the equipment rack 20.

Equipment rack 20 includes a stand 21 configured and operable for supporting various components for producing, storing and distributing the HOCl solution and the NaOH solution. Stand 21 is generally cuboid in shape and comprises a pair of side panels 22 with at least a bottom-shelf panel 23, a top-shelf panel 24 and a middle-shelf panel 25 disposed between the side panels 22. The middle-shelf panel 25 is located on the stand 21 medially between the bottom-shelf panel 23 and the top-shelf panel 24. The panels 22, 23, 24, 25 may be made of any suitable construction material, such as a metal material, a polymer-based material (e.g., plastic), a composite material, or a hybrid thereof. In an exemplary construction, panels 22, 23, 24, 25 are made of a heat formable metal material that is heated and formed (i.e., bent) to the contours of the stand 21. If desired, one or more of panels 22, 23, 24, 25 may be powder-coated for durability and aesthetic appearance. Panels 22 may be connected to panels 23, 24 and 25 in a conventional manner, such as with fasteners, rivets, adhesive, welding or the like. Furthermore, panels 22, 23, 24, 25 are provided with through holes, openings, guide channels, etc. as needed to route electrical cables, wiring and fluid conduits to and from the various components mounted on the stand 21, as will be described hereafter. If desired, the stand 21 may be provided with adjustable feet 26 for leveling and/or balancing the stand 21 on an uneven surface. Alternatively, the stand 21 may be provided with rollers, wheels, castors or the like (not shown)

to allow the stand 21 to be readily and conveniently moved from one location to another or to be positioned in a desired orientation.

In the Generation and Distribution Station Configuration the stand 21 supports a brine tank 30, an ECA solutions generator 40 and at least two ECA solution holding tanks 50, 60 on the equipment rack 20, as will be described in greater detail hereafter. The brine tank 30 defines an interior compartment (not shown) configured to receive a mixture of salt, such as high purity sodium chloride (NaCl) salt, and water ($H_2O$) from an external source of fresh water to form a suitable saltwater solution, commonly referred to as brine. In an arrangement of the Generation and Distribution Station Configuration shown in FIGS. 1-3, the brine tank 30 is supported on the bottom-shelf panel 23 adjacent one of the side panels 22 of the stand 21. If desired, the brine tank 30 may be mounted on or secured to the one side panel 22 and/or the bottom-shelf panel 23. Alternatively, the brine tank 30 may only be positioned against an L-shaped retaining bracket 27 (FIG. 2) provided on the upper surface of the bottom-shelf panel 23 to seat the brine tank 30 and prevent it from inadvertently being moved beyond the open rear of the stand 21. Regardless, the brine tank 30 is formed from a relatively lightweight, yet durable, chemically resistant, ultraviolet resistant and anti-corrosive polymer-based (plastic) or composite material. Brine tank 30 may have a removable cover 34 that permits access to the interior compartment for the purpose of adding the salt to the brine tank 30. The salt for the brine tank 30 is typically provided in the form of one or more salt blocks or salt pellets in a known manner. The brine tank 30 is in fluid (flow) communication with the ECA solutions generator 40, as will be described in greater detail hereafter, through a brine conduit 32 that extends from the brine tank 30 into the generator 40. The brine conduit 32 is likewise formed from a chemically resistant and anti-corrosive polymer-based (plastic) material, such as polyvinylchloride (PVC) tubing, that may be reinforced with spiral wound polyester yarn for increased strength and durability.

In an alternative arrangement of the Generation and Distribution Station Configuration of the equipment rack 20 shown in FIGS. 4-6, the brine tank 30 is supported on an auxiliary side shelf 28 attached to one of the side panels 22 of the stand 21. In the alternative arrangement, the auxiliary side shelf 28 is adjustably attached to the side panel 22 and has at least one height-adjustable support leg 29 as described more fully hereafter with reference to FIG. 11. In the Generation and Distribution Station Configuration, a gravity drain is needed to collect an overflow of the brine solution from the brine tank 30 and/or an overflow of an ECA solution from the ECA solution holding tanks 50, 60 through a drain line 36 that is in fluid (flow) communication with the brine tank 30 and the ECA solution holding tanks 50, 60. Consequently, in the absence of a conventional floor drain or in the event of an atypical floor drain, brine tank 30 is supported on the auxiliary side shelf 28 at a sufficient height above the floor instead of being supported on the bottom-shelf panel 23 of the stand 21. The adjustable side shelf 28 allows the brine tank 30 to be readily and conveniently positioned at a suitable height to allow gravity flow of any release of overflow from the brine tank 30 and/or the ECA solution holding tanks 50, 60 into an available collection container (not shown) or into a gravity drain in a utility sink, tub, P-trap or the like.

In the Generation and Distribution Station Configuration the equipment rack 20 may further include an optional conventional water filter 70 for filtering fresh water supplied to the equipment rack 20 from an external source of water through a conventional water line 72. As will be described hereafter, filtered water from water filter 70 is mixed with brine from brine tank 30 within the generator 40 to produce the ECA solutions. Alternatively, or in addition, fresh water may be supplied from the external source of water directly into the generator 40 through a separate water line (not shown). Filtered fresh water from water filter 70 may also be supplied to brine tank 30 to mix with the salt to produce the brine through a first water conduit 74 that extends from the water filter 70 to the brine tank 30. A second water conduit 76 extends from the water filter 70 to the generator 40 to supply filtered fresh water to the generator 40. As shown herein, the first water conduit 74 and the second water conduit 76 may be in flow communication with water filter 70 via a common connection, such as a conventional tee-coupling 75. First water conduit 74 may also be referred to as the brine tank water supply conduit and second water conduit 76 may also be referred to as the generator water supply conduit. As will be readily understood and appreciated by those skilled in the art, the amount of fresh water within the brine tank 30 may be regulated by a float sensor (not shown) disposed within the brine tank 30 in electrical and/or mechanical communication with the water filter 70 and the drain line 36 that extends from the brine tank 30 into the gravity drain.

The ECA solutions generator 40 is provided on the Generation and Distribution Station Configuration of the equipment rack 20 to produce cleaning, degreasing, sanitizing and disinfecting solutions from an EAW process. An example ECA solutions generator suitable for use with the Generation and Distribution Station Configuration of the equipment rack 20 in the present invention to produce an HOCl solution and an NaOH solution is shown and described in the United States Patent Application Publication No. 2022/0396505 A1, the disclosure of which is incorporated herein by reference. The ECA solutions generator 40 produces HOCl solution and NaOH solution from water, salt and electricity utilizing an electrolysis cell. In the exemplary embodiment of the Generation and Distribution Station Configuration shown and described herein, generator 40 comprises a housing 41 configured for containing an electrolysis cell (not shown) and various other electrical and mechanical components (not shown) for producing HOCl solution and NaOH solution utilizing fresh water from water filter 70 and brine from the brine tank 30. Electricity is provided to the generator 40 from an external source of AC power through a conventional power cable, power cord or the like 42. As previously mentioned, brine tank 30 has a brine conduit 32 in fluid (flow) communication with the generator 40 and water filter 70 has a generator water supply conduit (i.e., second water conduit 76) likewise in fluid (flow) communication with the generator 40. By way of example only and not limitation, the generator 40 may have at least one fluid pump, such as a peristaltic pump, for drawing the fresh water and/or the brine into the generator 40 from the water filter 70 and/or the brine tank 30, respectively. Regardless, the fresh water and the brine are mixed together within the generator 40 to produce a desired parts-per-million (ppm) concentration of free available chlorine (FAC) and the mixture is delivered to the electrolysis cell to generate an undiluted HOCl solution and an undiluted NaOH solution.

The generator 40 is supported on its underside by the top-shelf panel 24 of the stand 21. The generator 40 is also supported on its rear side by a first vertical panel 44 that extends upwardly from the top-shelf panel 24 at a medial location along the side panels 22. Consequently, the generator 40 is located at the top of the stand 21 and conveniently positioned to the front of the stand 21 in the Generation and Distribution Station Configuration of the equipment rack 20. As a result, the equipment rack 20 has an aesthetic appearance, especially when viewed from a side of the stand 21. A particular feature of the Generation and Distribution Station Configuration of the equipment rack 20 is that the first vertical panel 44 has an optional cutout 46 best seen in FIG. 2 and FIG. 5. The cutout 46 provides ready access to mounting fasteners on the rear of the generator through cutout 46 to allow various internal components of the generator 40 to be removed from the front side of the housing 41 without having to remove the entire generator 40 from the stand 21 of the equipment rack 20. Cutout 46 is shown in greater detail and further described herein with reference to FIG. 10. The generator 40 may have a hinged front cover 48 that is movable in an upward direction to provide access to internal components within the generator 40. Furthermore, various components of the generator 40 may be mounted on the front cover 48 for convenient access and/or information purposes. As sown herein by way of example and not limitation, an hour meter 49A, an on/off switch 49B and a pH monitor 49C may be mounted on the exterior of the front cover 48 of the generator 40.

The generator 40 is in fluid (flow) communication with the ECA holding tanks 50, 60 and the ECA solutions produced by the generator 40 are delivered to the ECA solution holding tanks 50, 60. In the Generation and Distribution Station Configuration of the equipment rack 20 shown and described herein, an HOCl solution produced by the generator 40 is delivered to holding tank 50 through an HOCl supply conduit 52 and an NaOH solution produced by the generator 40 is delivered to holding tank 60 through an NaOH supply conduit 62. The holding tanks 50, 60 are made of a lightweight, yet durable, chemically resistant, ultraviolet resistant and anti-corrosive polymer-based (plastic) or composite material, such as polyethylene or polypropylene. The holding tanks 50, 60 are generally hollow and may have any desired shape suitable for containing the HOCl solution and the NaOH solution. However, the holding tanks 50, 60 must be sized to be comfortably positioned between the side panels 22 of the stand 21. As shown herein, the holding tanks 50, 60 are supported on the middle-shelf panel 25 of the stand 21 and configured (sized and shaped) to be positioned between the side panels 22 of the stand 21 in a side-by-side orientation. A gravity nozzle, valve, spigot or the like 54, 64 is provided on the front side of the holding tanks 50, 60, respectively, for dispensing the HOCl solution from the holding tank 50 and the NaOH solution from the holding tank 60. The HOCl solution and the NaOH solution may be dispensed into a portable container, such as a spray bottle (not shown), for use at a location of a healthcare or food services facility, for example a hospital, nursing home, prison or school, to be cleaned, degreased, sanitized and/or disinfected with the HOCl solution and/or the NaOH solution. As best shown in FIG. 2 and FIG. 5, the holding tank 50, 60 are each provided with a drain line 56, 66, respectively, for discharging any overflow in the even the generator 40 delivers an excess of the ECA solution to the holding tank 50, 60. As illustrated herein, the drain lines 56, 66 from the holding tanks 50, 60 may be coupled together into a single drain line and subsequently coupled together with the drain line 36 from the brine tank 30 to minimize the number of drain line conduits present on the equipment rack 20 in the Generation and Distribution Station Configuration.

In the Generation and Distribution Station Configuration the equipment rack 20 may further include an optional dilution control station 80. As shown herein, the dilution control station 80 is mounted on a second vertical panel 82 between the top-shelf panel 24 and the middle-shelf panel 25. As such, the dilution control station 80 is located below the generator 40 and in front of the holding tanks 50, 60. The dilution control station 80 is configured and operable to dilute the HOCl solution and the NaOH solution produced by the generator 40 and stored in the HOCl holding 50 and the NaOH holding tank 60 to various strength cleaning, degreasing, sanitizing and disinfecting solutions. As shown in FIG. 2 and FIG. 5, a plurality of fluid conduits is provided from the holding tanks 50, 60 into the dilution control station 80, for example, through an opening formed through the second vertical panel 82. In the embodiment illustrated herein, two fluid conduits extend from the HOCl holding tank 50 into the dilution control station 80 and three fluid conduits extend from the NaOH holding tank 60 into the dilution control station 80. The fluid conduits and the opening are not numbered in the accompanying drawing figures for purposes of clarity. A selection dial 84 may be provided on the front side of dilution control station 80 for selecting various strengths of diluted HOCl solution and NaOH solution. By way of example and not limitation, selection dial 84 may be configured to select one of an all-purpose cleaner, a glass and chrome cleaner, a daily disinfectant and a sanitizer. The dilution control station 80 may be further provided with a pair of dispensing buttons 86 and a pair of corresponding gravity nozzles, valves, spigots, tubes or the like 88 for dispensing the various strengths of diluted HOCl solution and NaOH solution from the dilution control station 80.

Figure 7:
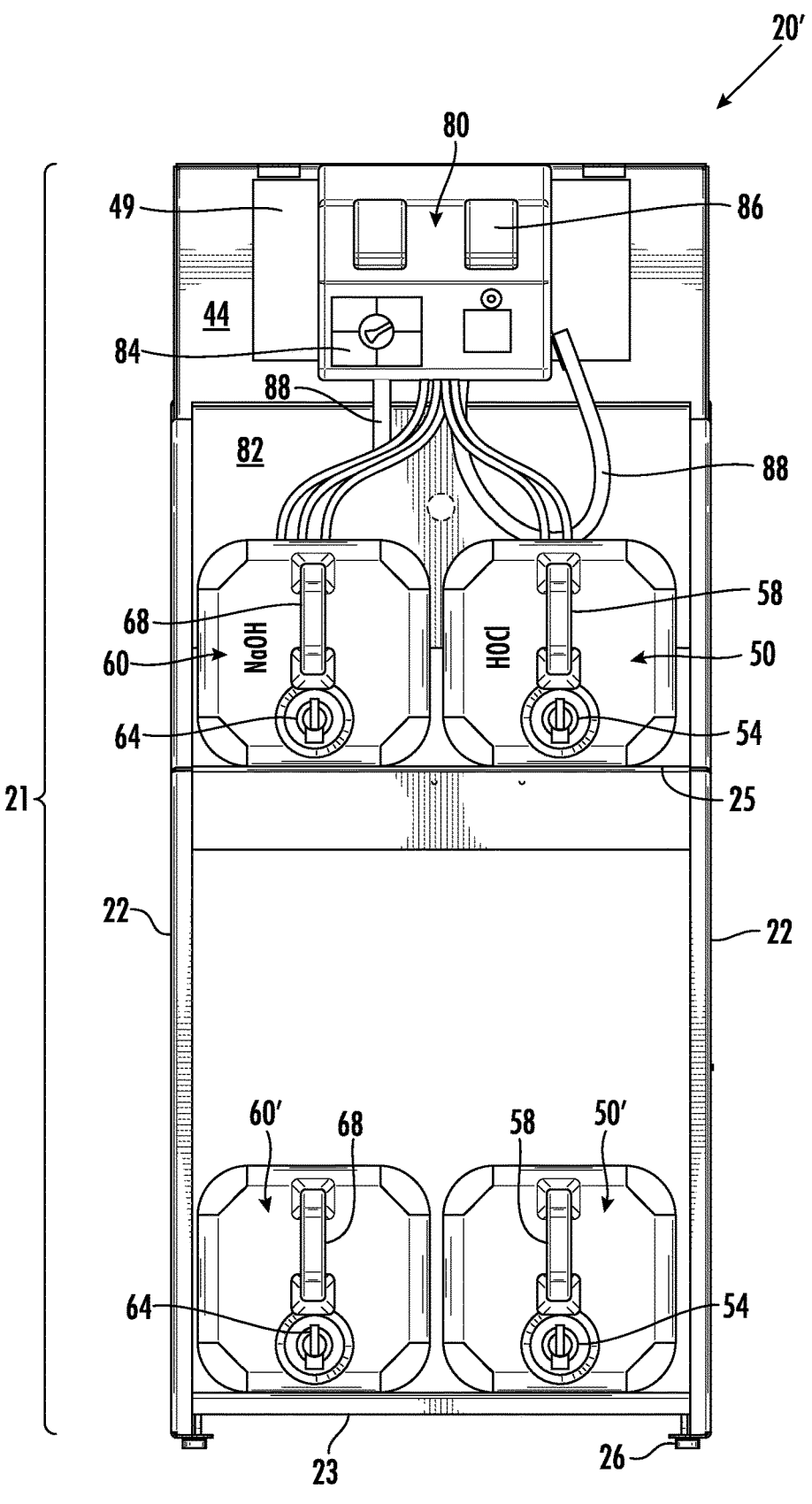
FIG. 7 is a front elevation view of an exemplary embodiment a multi-function equipment rack for storing and distributing ECA solutions according to the present invention.
Figure 8:
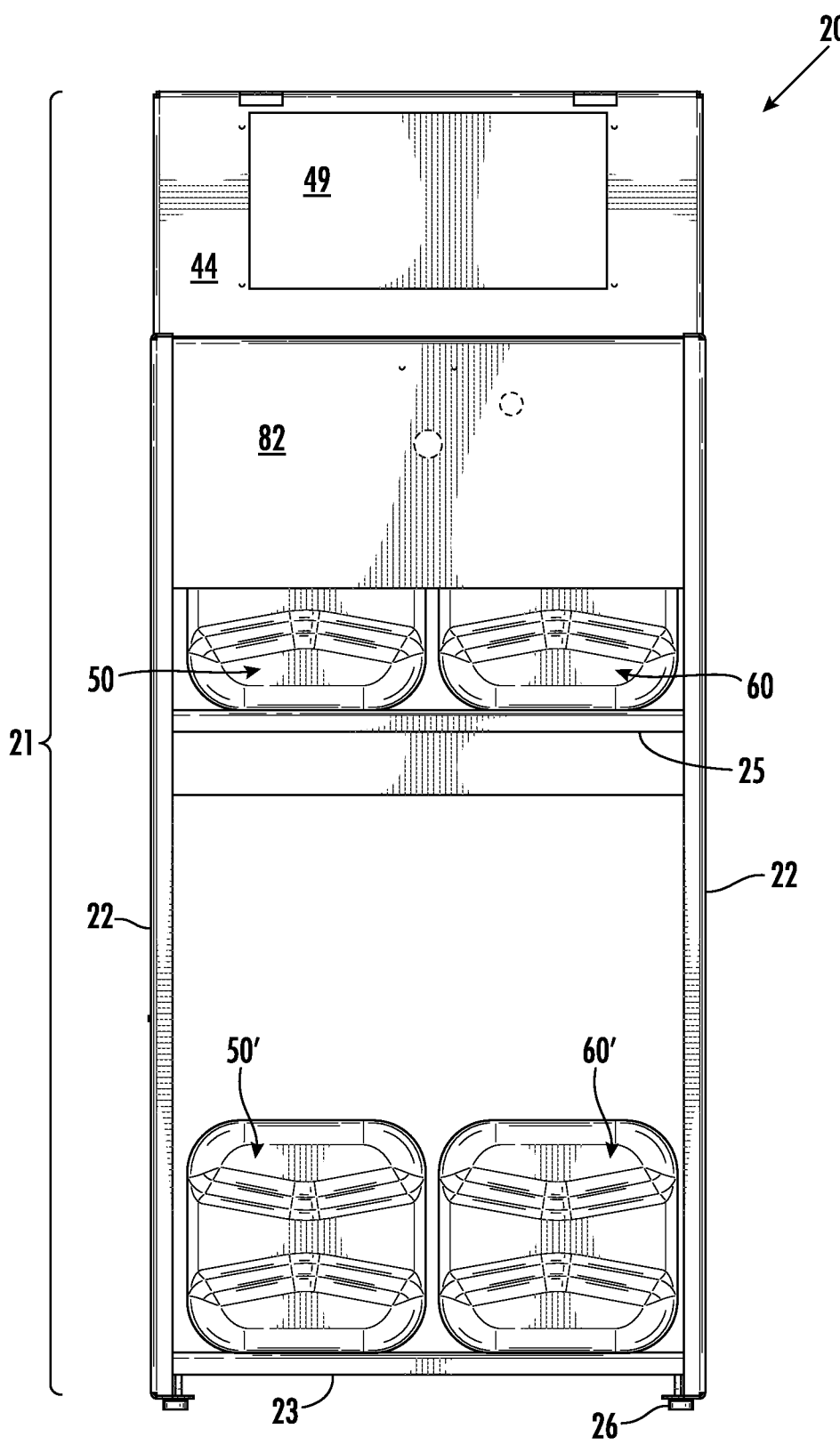
FIG. 8 is a rear elevation view of the multi-function equipment rack of FIG. 7.
Figure 9:
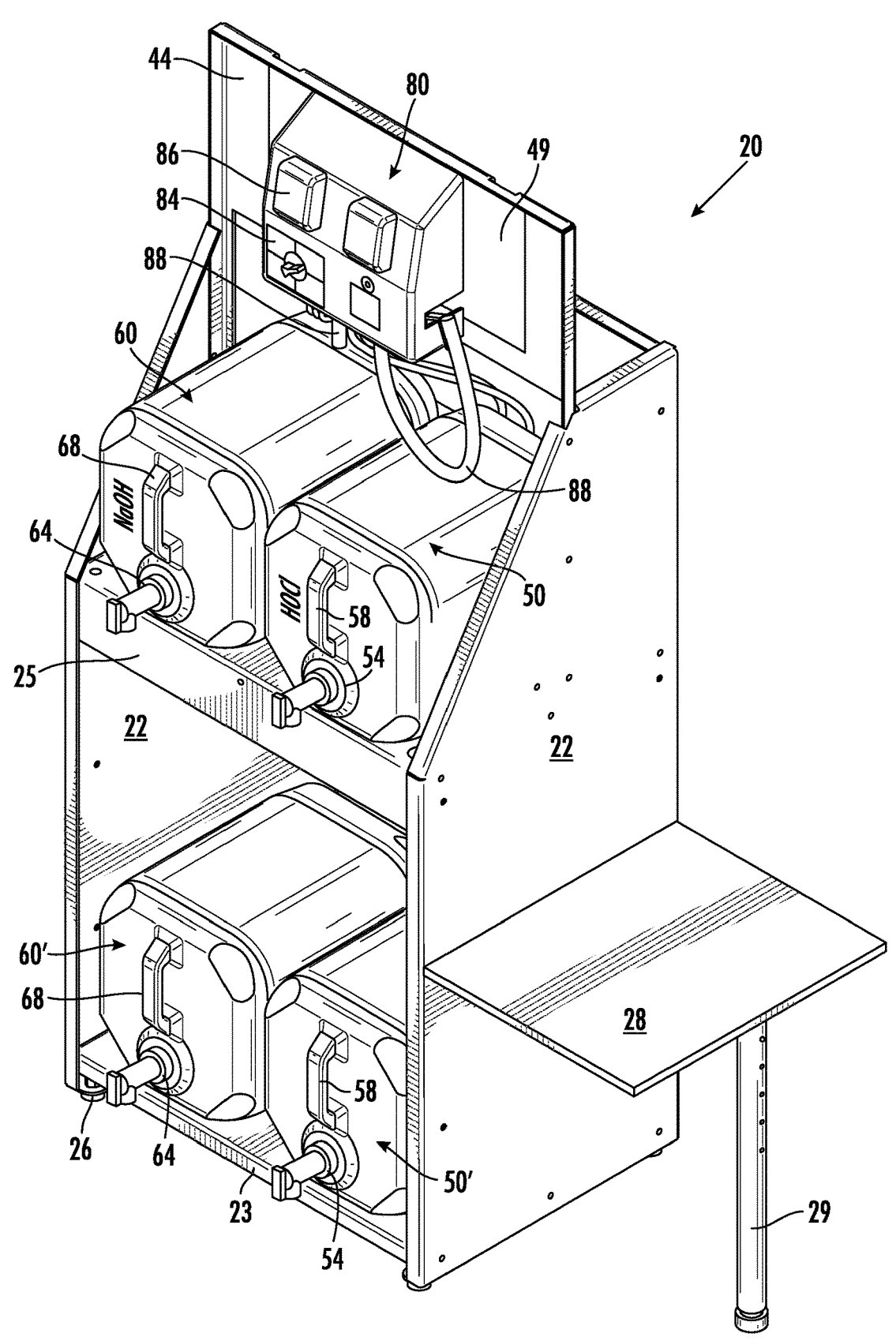
FIG. 9 is a front perspective view of the multi-function equipment rack of FIG. 7 shown in an alternative arrangement.

FIGS. 7-9 show another exemplary embodiment of an apparatus, system and method for storing and distributing ECA solutions according to the present invention. Specifically, FIGS. 7-9 illustrate a multi-function equipment rack, indicated generally by reference character 20', in a Distribution Station Configuration for storing and distributing ECA solutions, such as an HOCl solution and an NaOH solution. For purposes of reference, FIG. 7 is a front elevation view, FIG. 8 is a rear elevation view, and FIG. 9 is a front perspective view of the equipment rack 20' in the Distribution Station Configuration. The equipment rack 20' includes the stand 21 previously described configured and operable for supporting various components for storing and distributing the HOCl solution and the NaOH solution. It should be noted that in the Distribution Station Configuration the stand 21 is reversed, i.e., turned around or rotated 180 degrees relative to the orientation of the stand 21 in the Generation and Distribution Station Configuration. Otherwise, all structural components of stand 21 are in the same location and configuration. Specifically, panels 22, 23, 24, 25, first vertical panel 44 and second vertical panel 82 are identical on the Generation and Distribution Station Configuration of the equipment rack 20 and on the Distribution Station Configuration of the equipment rack 20'. The equipment rack of the present invention is referred to as a "multi-function" equipment rack because the same stand 21 can be used in either the Generation and Distribution Station Configuration or the Distribution Station Configuration with minimal modifications.

The difference between the equipment rack 20 and the equipment rack 20' in the Distribution Station Configuration is merely the components that are supported on the stand 21 and, in certain instances, the location of the components on the stand 21. Specifically, the Generation and Distribution Station Configuration of the equipment rack 20 includes the ECA solutions generator 40 for the producing ECA solutions, namely, the HOCl solution and the NaOH solution. The Distribution Station Configuration of the equipment rack 20' includes only the ECA solutions, namely the HOCl solution and the NaOH solution, and the dilution control station 80 previously described. Consequently, the equipment rack 20' is configured for storing and distributing ECA solutions at a satellite location separate from the location at which the ECA solutions were produced. By way of example and not limitation, the ECA solutions may be produced at a separate location on-site, or alternatively, may be produced at a remote manufacturing site and delivered to the facility to be cleaned and degreased or sanitized and disinfected. Furthermore, the ECA solutions may be produced utilized the generator 40 previously described in an EAW process or with any other apparatus, device, system and/or method. Since the Distribution Station Configuration of the equipment rack 20' only stores and distributes full strength ECA solutions and distributes ECA solutions diluted by dilution control station 80, the brine tank 30, generator 40 and water filter 70 components previously described with reference to the Generation and Distribution Station Configuration of the equipment rack 20 are not included with the equipment rack 20'.

FIGS. 7 and 8 show an arrangement of the equipment rack 20' in the Distribution Station Configuration including ECA solution holding tanks 50, 60 and dilution control station 80. Holding tanks 50, 60 are essentially as previously described in structure and function, and therefore, need not be described here in detail. It should be noted, however, that each of the holding tanks 50, 60 included with the equipment rack 20' in the Distribution Station Configuration may be provided with a handle 58, 68, respectively, configured for conveniently transporting the holding tanks 50, 60 to the equipment rack 20'. As illustrated herein, the holding tanks 50, 60 are supported on the middle-shelf panel 25 of the stand 21 in front of the second vertical panel 82. However, since the orientation of the stand 21 is reversed, the holding tanks 50, 60 are likewise reversed in orientation relative the holding tanks 50, 60 on the equipment rack 20 in the Generation and Distribution Station Configuration. If desired, additional auxiliary holding tanks 50', 60' may be provided on the equipment rack 20' and supported on the bottom-shelf panel 23. The auxiliary holding tanks 50', 60' replace depleted (empty) holding tanks 50, 60 to avoid any interruption in the availability of the ECA solutions on the equipment rack 20' in the Distribution Station Configuration.

As best shown in FIG. 7, the dilution control station 80 is supported on the front side of the first vertical panel 44 above the ECA solution holding tanks 50, 60 that are supported on the middle-shelf panel 25 in front of the second vertical panel 82. The previously mentioned fluid conduits extend downwardly from the dilution control station 80 to the ECA solution holding tanks 50, 60. As illustrated herein, two fluid conduits extend from the dilution control station 80 to the HOCl holding tank 50 and three fluid conduits extend from the dilution control station 80 to the NaOH holding tank 60. As previously mentioned, the dilution control station 80 is provided with a selection dial 84, a pair of dispensing buttons 86 and a corresponding pair of gravity nozzles, valves, spigots, tubes or the like 88 for dispensing the various strengths of diluted HOCl solution and NaOH solution from the dilution control station 80.

FIG. 9 shows an alternative arrangement of the equipment rack 20' in the Distribution Station Configuration including ECA solution holding tanks 50, 60 and dilution control station 80. The holding 50, 60 and auxiliary holding tanks 50', 60', and the dilution control station 80 are essentially as previously described in structure and function, and therefore, need not be described here in detail. However, in the alternative arrangement, the equipment rack 20' includes an auxiliary side shelf 28 adjustably attached to one of the side panels 22 of the stand 21 and at least one height-adjustable support leg 29 as previously described with reference to FIG. 6 and as will be described more fully hereafter with reference to FIG. 11. In the alternative arrangement of the Distribution Station Configuration of the equipment rack 20', another auxiliary holding tank 50' of the HOCl solution and/or another auxiliary holding tank 60' of the NaOH solution may be stored on the side shelf 28. Alternatively, the side shelf 28 may be used to store and support cleaning supplies or other items associated with the Distribution Station Configuration of the equipment rack 20'.

Figure 10:
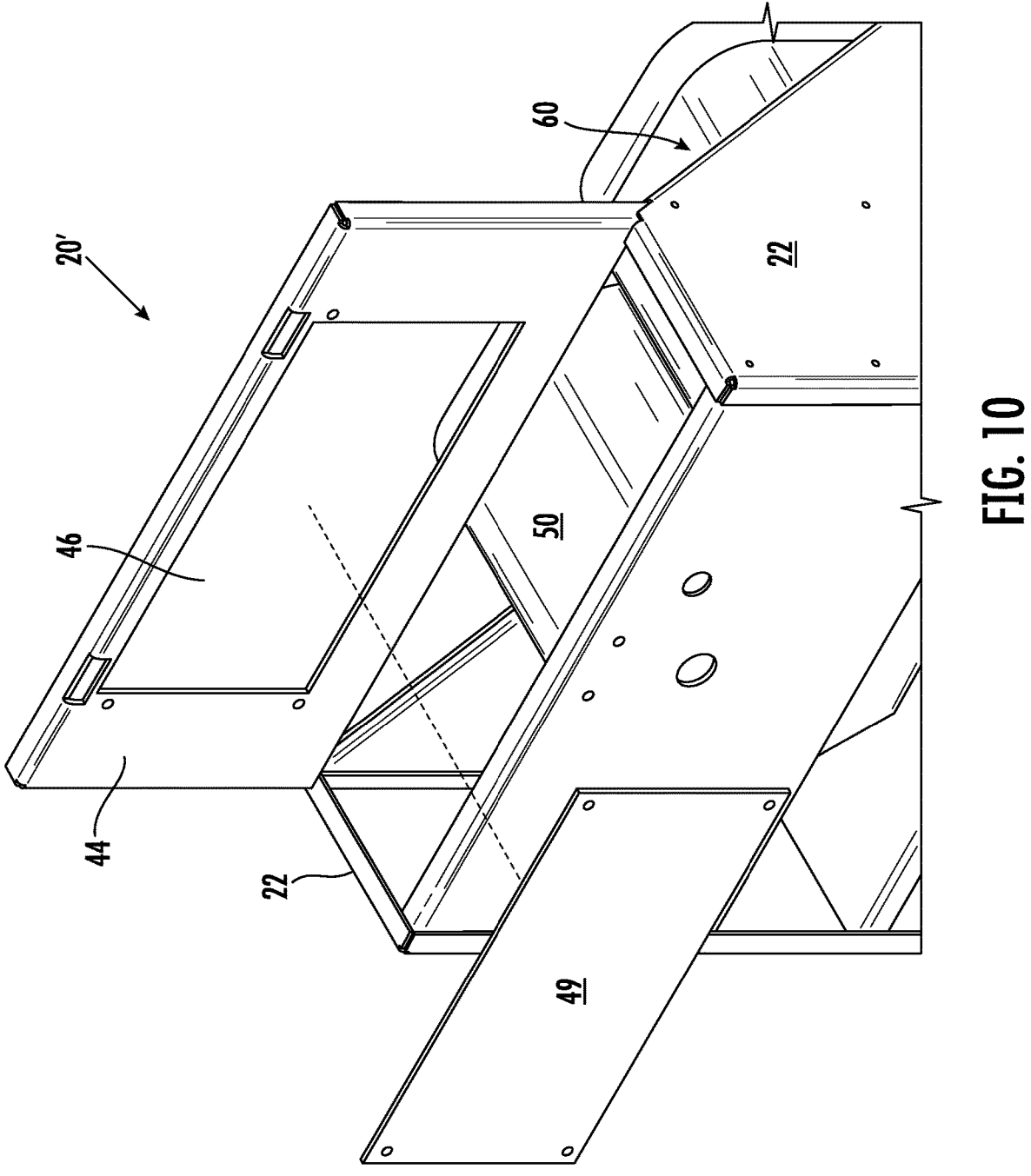
FIG. 10 is a partial rear perspective view of the multi-function equipment rack of FIG. 7 showing a removable cover plate in greater detail.

FIG. 10 is a partial rear perspective view of the equipment rack 21' of the Distribution Station Configuration in greater detail. FIG. 10 shows a removable cover plate 49 configured and operable for covering the cutout 46 that allows internal components of the generator 40 to be removed without having to remove the entire generator 40 from the stand 21 in the Generation and Distribution Station Configuration of the equipment rack 20. The removable cover plate 49 is secured to the rear side of the first vertical panel 44, for example with fasteners, to provide a mounting surface on the front side of the first vertical panel 44 to mount the dilution control station 80 in the Distribution Station Configuration of the equipment rack 20'.

Figure 11:
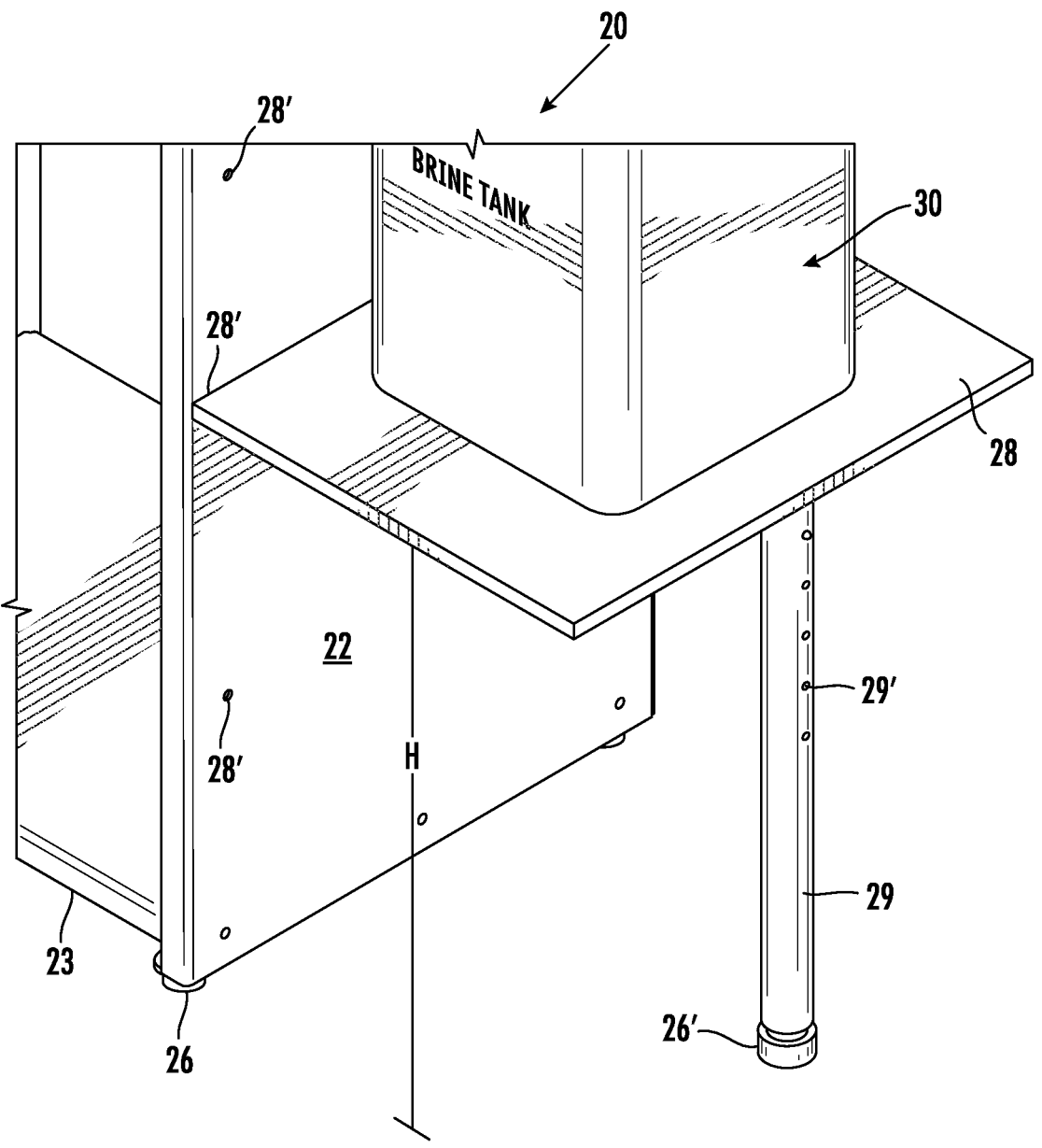
FIG. 11 is a partial front perspective view of the multi-function equipment rack of FIG. 6 showing the alternative arrangement in greater detail.

FIG. 11 is a partial front perspective view of the equipment rack 20 in the alternative arrangement of the Generation and Distribution Station Configuration in greater detail. FIG. 11 shows the auxiliary side shelf 28 attached to one of the side panels 22 of the stand 21 at a sufficient height for the drain line 36 of the brine tank 30 to be routed into a suitable collection container (not shown) or into a gravity drain in a utility sink, tub, P-trap or the like in the event a conventional floor drain is not available. The auxiliary side shelf 28 is adjustable attached to the side panel 22 of the stand 21 at one of a plurality of locations 28' vertically spaced apart on the side panel 22. In this manner, the auxiliary side shelf 28 can be positioned at a vertical height H above the floor sufficient for any overflow from the brine tank 30 or the holding tanks 50, 60 to be discharged through the drain line 36 into the gravity drain. The auxiliary side shelf 28 is provided with a height-adjustable support leg 29. As illustrated herein, the support leg 29 has a telescoping inner sleeve and a plurality of holes 29' formed in an outer sleeve. A biased (e.g., spring biased) rod, ball or the like (not shown) is received within one of the holes 29' to lock the support leg 29 at the desired vertical height H of the auxiliary side shelf 28 in a known manner. If desired, the support leg may be provided with an adjustable foot 26' for leveling and/or balancing the auxiliary side shelf 28.

The foregoing detailed description of exemplary embodiments of the apparatus, system and method for a multifunctional equipment rack is merely illustrative of the general concepts and principles of the present invention. Regardless of the foregoing detailed description and illustrated embodiments, various other configurations of the apparatus, system and method, as well as reasonable equivalents thereof, will be readily apparent and understood by those having ordinary skill in the art. Accordingly, equivalents to those shown in the accompanying drawing figures and described in the written description are intended to be encompassed by the broadest reasonable interpretation and construction of the appended claims. Furthermore, as numerous modifications to the exemplary embodiments will readily occur to those skilled in the art, the present invention is not to be limited to the specific configuration, construction, materials, manner of use and operation shown and described herein. Instead, all reasonably predictable and suitable equivalents and obvious modifications to the present invention should be determined to fall within the scope of the appended claims given their broadest reasonable interpretation and construction in view of the accompanying written description and drawing figures in view of the combined teachings of the disclosures of the relevant prior art.

That which is claimed is:

1. A multi-function equipment rack for electrochemically activated (ECA) solutions, the equipment rack comprising:
   a stand;
   wherein the equipment rack is structured to configure in a first configuration and in a second configuration that is different than the first configuration;
   wherein the first configuration of the equipment rack includes the stand, a brine tank for containing a brine solution, a generator in fluid communication with the brine tank for producing at least one ECA solution from the brine solution, at least one ECA solution holding tank in fluid communication with the generator for containing the at least one ECA solution, and a dilution control station in fluid communication with the at least one ECA solution holding tank for diluting the at least one ECA solution;
   wherein the second configuration of the equipment rack includes the stand, the at least one ECA solution holding tank for containing the at least one ECA solution, and the dilution control station in fluid communication with the at least one ECA solution holding tank for diluting the at least one ECA solution;
   wherein the stand further has a cutout and a removable cover for covering the cutout; and
   wherein in the first configuration the cutout provides access to the generator and in the second configuration the removable cover provides a mounting surface for the dilution control station when the removable cover covers the cutout.

2. The multi-function equipment rack according to claim 1, wherein the at least one ECA solution comprises at least one of a hypochlorous acid (HOCl) solution and a sodium hydroxide (NaOH) solution.

3. The multi-function equipment rack according to claim 1, wherein the generator produces the at least one ECA solution utilizing an electrochemically activated water (EAW) process.

4. The multi-function equipment rack according to claim 1, wherein the stand comprises a pair of side panels and a bottom-shelf panel disposed between the pair of side panels, and wherein the brine tank is supported on the bottom-shelf panel in the first configuration.

5. The multi-function equipment rack according to claim 1, wherein the stand comprises a pair of side panels and a top-shelf panel disposed between the pair of side panels, and wherein the generator is supported on the top-shelf panel in the first configuration.

6. The multi-function equipment rack according to claim 1, wherein the stand comprises a pair of side panels and a middle-shelf panel disposed between the pair of side panels, and wherein the at least one ECA solution holding tank is supported on the middle-shelf panel in the first configuration and in the second configuration.

7. The multi-function equipment rack according to claim 1, wherein the stand comprises a pair of side panels and a first vertical panel disposed between the pair of side panels, and wherein the generator is positioned adjacent the first vertical panel in the first configuration.

8. The multi-function equipment rack according to claim 7, wherein the stand further comprises a second vertical panel disposed between the pair of side panels, and wherein the dilution control station is positioned adjacent the second vertical panel in the first configuration.

9. The multi-function equipment rack according to claim 1, wherein the stand comprises a pair of side panels and a first vertical panel disposed between the pair of side panels, and wherein the dilution control station is positioned adjacent the first vertical panel in the second configuration.

10. The multi-function equipment rack according to claim 1, wherein the stand comprises a pair of side panels, an auxiliary side shelf attached to one of the pair of side panels, and a height-adjustable support leg for supporting the auxiliary side shelf.

11. The multi-function equipment rack according to claim 10, wherein the brine tank is supported on the auxiliary side shelf in the first configuration.

12. The multi-function equipment rack according to claim 1, wherein the equipment rack in the first configuration further includes a water filter in fluid communication with an external source of water, in fluid communication with the brine tank, and in fluid communication with the generator.

13. A multi-function equipment rack for producing, storing and distributing electrochemically activated (ECA) solutions, the equipment rack comprising:
   a stand comprising a pair of side panels, a bottom-shelf panel disposed between the pair of side panels, a top-shelf panel disposed between the pair of side panels, a middle-shelf panel disposed between the pair of side panels and medially between the bottom-shelf panel and the top-shelf panel, a first vertical panel disposed between the pair of side panels and extending upwardly from the top-shelf panel, and a second vertical panel disposed between the pair of side panels and between the top-shelf panel and the middle-shelf panel;
   a brine tank supported on the bottom-shelf panel for containing a brine solution;
   a generator supported on the top-shelf panel adjacent the first vertical panel, the generator in fluid communication with the brine tank for producing at least one ECA solution;
   at least one ECA solution holding tank supported on the middle-shelf panel and in fluid communication with the generator; and
   a dilution control station supported on the middle-shelf panel or alternatively adjacent the second vertical panel, the dilution control station in fluid communication with the at least one ECA solution holding tank;
   wherein the first vertical panel defines a cutout formed therethrough; and
   a removable cover plate configured to cover the cutout from a rear side of the first vertical panel and to provide access to the generator from the rear side of the first vertical panel when the cover plate is removed.

14. The multi-function equipment rack according to claim 13, wherein the generator produces the at least one ECA solution from the brine solution utilizing an electrochemically activated water (EAW) process, and wherein the at least one ECA solution comprises at least one of a hypochlorous acid (HOCl) solution and a sodium hydroxide (NaOH) solution.

15. The multi-function equipment rack according to claim 13, wherein the stand further comprises an auxiliary side shelf attached to one of the pair of side panels and a height-adjustable support leg for supporting the auxiliary side shelf.

16. The multi-function equipment rack according to claim 13, wherein the equipment rack further includes a water filter in fluid communication with an external source of water, in fluid communication with the brine tank, and in fluid communication with the generator.

17. A multi-function equipment rack for storing and distributing electrochemically activated (ECA) solutions, the equipment rack comprising:

a stand comprising a pair of side panels, a top-shelf panel disposed between the pair of side panels, a middle-shelf panel disposed between the pair of side panels, and a first vertical panel disposed between the pair of side panels and extending upwardly from the top-shelf panel;

at least one ECA solution holding tank supported on the middle-shelf panel for containing an ECA solution; and a dilution control station supported on the first vertical panel, the dilution control station in fluid communication with the at least one ECA solution holding tank;

wherein the first vertical panel defines a cutout formed therethrough; and a removable cover plate configured to cover the cutout from a rear side of the first vertical panel and to provide a mounting surface for the dilution control station on a front side of the first vertical panel when the cover plate covers the cutout.

18. The multi-function equipment rack according to claim 17, wherein the at least one ECA solution is selected from a hypochlorous acid (HOCl) solution and a sodium hydroxide (NaOH) solution.

19. The multi-function equipment rack according to claim 17, wherein the stand further comprises an auxiliary side shelf attached to one of the pair of side panels and a height-adjustable support leg for supporting the auxiliary side shelf.

* * * * *